United States Patent [19]

Hung et al.

[11] Patent Number: 5,866,711
[45] Date of Patent: Feb. 2, 1999

[54] FLUOROCYANATE AND FLUOROCARBAMATE MONOMERS AND POLYMERS THEREOF

[75] Inventors: Ming-Hong Hung, Wilmington, Del.; Paul Douglas Brothers, Chadds Ford; Dewey Lynn Kerbow, Landenberg, both of Pa.

[73] Assignee: E. I. du pont de Nemours and Company, Wilmington, Del.

[21] Appl. No.: 898,909

[22] Filed: Jul. 23, 1997

Related U.S. Application Data

[60] Provisional application No. 60/026,089 Sep. 13, 1996.
[51] Int. Cl.⁶ .................................................. C07C 261/00
[52] U.S. Cl. .............................. 560/167; 560/301
[58] Field of Search ...................... 560/167, 301

[56] References Cited

U.S. PATENT DOCUMENTS

| | | | |
|---|---|---|---|
| 3,681,292 | 8/1972 | Loudas et al. | 560/301 |
| 3,733,349 | 5/1973 | Loudas et al. | 560/301 |
| 3,761,501 | 9/1973 | Woolf et al. | 560/301 |
| 4,281,091 | 7/1981 | Strazik et al. | 525/518 |
| 4,281,092 | 7/1981 | Breazeale | 526/247 |
| 4,564,717 | 1/1986 | Ohmori et al. | 568/843 |
| 5,059,720 | 10/1991 | Hung | 568/674 |
| 5,266,639 | 11/1993 | Chapman et al. | 525/200 |
| 5,328,946 | 7/1994 | Tuminello et al. | 524/462 |

FOREIGN PATENT DOCUMENTS

| | | | |
|---|---|---|---|
| 0244251 | 10/1960 | Australia | 560/167 |
| 0625613 | 6/1963 | Belgium | 560/167 |
| 0676637 | 12/1963 | Canada | 560/167 |
| 0891567 | 3/1962 | United Kingdom | 560/167 |
| 1231946 | 5/1971 | United Kingdom | 560/167 |

*Primary Examiner*—Jeffrey T. Smith
*Assistant Examiner*—N. Sarofim

[57] ABSTRACT

Fluorinated vinyl ethers having cyanate or carbamate groups are useful as monomers in making fluoropolymers having functional sites.

5 Claims, No Drawings

FLUOROCYANATE AND FLUOROCARBAMATE MONOMERS AND POLYMERS THEREOF

RELATED APPLICATIONS

This application claims the benefit of Provisional Application Ser. No. 60/026,089, filed Sep. 13, 1996.

FIELD OF THE INVENTION

This invention is in the field of fluorinated compounds useful as monomers in making fluoropolymers.

BACKGROUND OF THE INVENTION

There is an increasing demand for functionalized fluoromonomers and polymers to be applied in the areas of adhesion enhancement, cured coatings, interface compatibilizers for compounding/blending, and so on. Known cyano-containing cure site monomers such as $CF_2=CFOCF_2CF(CF_3)OCF_2CF_2$—CN (8-CNVE, U.S. Pat. No. 4,281,092) used in perfluoroelastomers require high temperature and the presence of catalysts to complete the curing. Hence, the direct utilization of functional monomers such as 8-CNVE in fluoroplastics is generally inconvenient to use and not practical.

Thus, there is an unfilled need for convenient functional monomers for use in fluoropolymers.

SUMMARY OF THE INVENTION

This invention provides compounds having the formula $$CF_2=CF-R_f-(CH_2)_n-X \quad (I)$$

wherein —X is —OCN (cyanate) or —O—(CO)—NH$_2$ (carbamate), n is 1–3, and R$_f$ is perfluoroalkyl or perfluoroalkoxy having 1–20 carbon atoms.

Polymers comprising units derived from compound (I) are also provided. Preferred polymers contain units derived from at least one other fluoromonomer. Thus, this invention provides polymers having at side groupS —R$_f$—(CH$_2$)$_n$—X, wherein —X is at least one of —OCN and —O—(CO)—NH$_2$. The presence of such groups can transform the normally chemically inert fluoropolymer into a reactive fluoropolymer to enhance its adhesion to other materials.

DETAILED DESCRIPTION

It has been discovered that compounds having the formula $$CF_2=CF-R_f-(CH_2)_n-X \quad (I)$$

wherein —X is —OCN or —O—(CO)—NH$_2$, n is 1–3, and R$_f$ is linear or branched perfluoroalkyl or perfluoroalkoxy having 1–20 carbon atoms are useful as monomers in making fluoropolymers, and are particularly useful in minor amount to introduce highly reactive functional side groups into the fluoropolymer. Such fluoropolymers are useful materials in the areas of adhesion enhancement, coatings, thermosetting resins, grafting polymers, curable elastoplastics and elastomers, and the like.

The new functional fluorinated compounds (I) wherein —X is —OCN, i.e., cyanates, can be synthesized by reacting compounds of the general formula $CF_2=CF-R_f-(CH_2)_n$—OH with CNY, Y=Br or Cl, to obtain $$CF_2=CF-R_f-(CH_2)_n-OCN \quad (II)$$

It has also been discovered that the cyanate can be hydrolyzed under acidic conditions to obtain the new functional fluorinated compounds (I) wherein —X is —O—(CO)—NH$_2$, i.e., carbamates having the formula $$CF_2=CF-R_f-(CH_2)_n-O-(CO)-NH_2 \quad (III)$$

In compounds (I), preferably n=1. Preferred R$_f$ are perfluoroalkoxy having 2–20 carbon atoms, including [O—CF$_2$CF(CF$_3$)]$_k$—O—CF$_2$CF$_2$ wherein k=1–5, most preferably k=1, and O—(CF$_2$)$_m$ wherein m=2–20, most preferably m=2–4. When R$_f$ is (CF$_2$)$_j$, j=1–12. Preferably, j=2–8.

The cyanate compound $CF_2=CF-R_f-(CH_2)_n$—OCN (II) of this invention exhibits an unusual combination of properties. Hydrolytic stability of the cyanate is good under neutral conditions and even under acidic conditions at ambient temperature, thereby making it possible to use (I) wherein —X is —OCN in controlled aqueous polymerization processes, as well as in non-aqueous processes, to obtain polymers with side groups containing the cyanato group (—OCN). However, under acidic conditions at elevated temperature, the cyanate can be converted to the carbamate compound $CF_2=CF-R_f-(CH_2)_n-O-(CO)-NH_2$ (III). The carbamate compound can also be used in polymerization processes to obtain polymers with side groups containing the carbamate group (—OCONH$_2$). Furthermore, the unique combination of conditions under which the cyanate hydrolyzes to the carbamate and the acidic nature and/or elevated temperature of aqueous polymerization of fluoromonomers makes it possible to introduce (II) into polymerization and to obtain polymer with side groups containing the carbamate group, i.e., to hydrolyze some of the —OCN to —O—(CO)—NH$_2$ during the polymerization process. This is illustrated by Example 12 below. Nevertheless, the compounds (I) are thermally active enough to provide rapid crosslinking at moderate temperatures, making them useful, for example, as crosslinking sites in polymers. Additionally, the functionality of (I) can be used to provide fluoropolymers, which are normally non-adherent, with adhesive properties. In either case, the functional comonomer units in the copolymer may be changed from the original comonomer, but are nevertheless derived therefrom.

The unusual temperature response of (I) has several implications for utility, such as when used as a monomer incorporated into fluoropolymers. Because of its high thermal activity, (I) can be very useful as a monomer in polymer resins that are fabricated without high temperature exposure before shaping, as in powder coating or in deposition from solution or aqueous dispersion, or in polymers that can be shaped by melt processing techniques at relatively low temperature and subsequently cured, such as for low-melting polymers or for elastomeric polymers.

Cyanates (II) of this invention can be prepared in high yield by a one-step process in which compounds having the general formula $$CF_2=CF-R_f-(CH_2)_n-OH \quad (IV)$$

wherein n and R$_f$ are as defined above, are reacted with cyanogen bromide (CNBr) or cyanogen chloride (CNCl) in the presence of base. Starting compounds (IV) are known, and are disclosed, for example, in U.S. Pat. Nos. 4,564,717 and 5,059,720. Bases that can be used are non-nucleophilic bases including tertiary amines such as trialkylamines, e.g., triethylamine; cyclic amines such as 1,8-bis(methylamino) naphthalene, morpholine, and N-methylmorpholine; 1,8-diazabicyclo[5.4.0]undec-7-ene (DBU); 1,5-diazabicyclo[4.3.0]non-5-ene (DBN); and the like. In carrying out the reaction, it is preferred for the cyanogen halide and the base each to be present in an amount slightly in excess of the amount of (IV) on a molar basis. Large excesses of base and/or cyanogen halide can be used but are not necessary. The reaction can be carried out at atmospheric pressure under essentially anhydrous conditions in a convenient medium that is stable toward non-nucleophilic base such as acetone, tetrahydrofuran, or ethyl ether. Reaction temperature is not critical, but the reaction is exothermic and the heat of reaction is desirably removed by appropriate cooling means. Preferably, the reaction is carried out at temperature below room temperature, most preferably at about 0°–10° C. which is conveniently achieved with ice water.

Carbamates (III) of this invention can be prepared from the cyanates (II) by contacting the cyanate with acid at elevated temperature for time sufficient to complete conversion of cyanate to carbamate. Suitable acids include hydrochloric, nitric, sulfuric, and other common inorganic acids. Temperature is desirably at least 30° C. but less than 100° C., preferably in the range 40°–75° C.

The processes for making the cyanates (II) and the carbamates (III) are further aspects of the invention.

Polymers of this invention comprise units derived from compound (I) of this invention. Preferred polymers of this invention contain units derived from at least one other fluorinated monomer, though such polymers can also contain units derived from fluorine-free monomers. Fluorinated monomers that can be used generally contain at least 35 wt % fluorine and include fluoroolefins having 2–10 carbon atoms, fluorinated dioxoles, and fluorinated vinyl ethers of the formula $CY_2=CYOR$ or $CY_2=CYOR'OR$ wherein Y is H or F, and —R and —R'— are independently completely-fluorinated or partially-fluorinated alkyl and alkylene groups containing 1–8 carbon atoms. Preferred —R groups contain 1–4 carbon atoms and are preferably perfluorinated. Preferred —R'— groups contain 2–4 carbon atoms and are preferably perfluorinated. Preferred fluoroolefins have 2–6 carbon atoms and include TFE, HFP, CTFE, vinyl fluoride, vinylidene fluoride, trifluoroethylene, hexafluoroisobutylene, and perfluorobutyl ethylene. Preferred cyclic fluorinated monomers include perfluoro-2,2-dimethyl-1,3-dioxole (PDD) and perfluoro-2-methylene-4-methyl-1,3-dioxolane (PMD). Preferred fluoropolymers include the group of tetrafluoroethylene (TFE) polymers. Preferred TFE polymers include perfluoropolymers, particularly copolymers of TFE and one or more of perfluoroolefins having 3–8 carbon atoms, especially hexafluoropropylene (HFP), and perfluoro(alkyl vinyl ethers) having alkyl groups containing 1–5 carbon atoms, especially 1–3 carbon atoms. Preferred fluoropolymers also include melt-fabricable copolymers of ethylene and TFE or chlorotrifluoroethylene, which copolymers can also contain up to 10 mol % of one or more additional monomers.

Copolymerizable fluorine-free monomers that can be used in conjunction with the cyanate or carbamate of this invention and at least one other fluorinated monomer include, for example, ethylene, propylene, n-butylene, iso-butylene, vinyl acetate, and vinyl ethers such as methyl vinyl ether.

Such fluoropolymers can be glassy, plastic, or elastomeric. They can be amorphous or partially crystalline, melt-fabricable or non-melt-fabricable. Melt-fabricable fluoropolymer resins, usually having melt viscosity of up to about $1 \times 10^5$ Pa·s as customarily measured, are usually considered to be extrudable or injection-moldable. The fluoropolymers of this invention are normally solid at 15°–20° C. and can have any molecular weight (MW) suitable for the intended use. Generally, the weight average MW is at least 50,000 and can range up to much higher values, such as 1,000,000 and even higher.

For fluoropolymers of this invention comprising (I) and at least one other fluorinated monomer, units derived from compounds (I) are usually minor components of the polymers. Generally, the amount of (I) is in the range 0.02–10 mol % based on total monomer units in the polymer. Preferably, the amount of (I) is 0.02–5 mol %, most preferably 0.02–3 mol %.

The identity and proportion in the polymer of units derived from other monomers, fluorinated and fluorine-free, can have wide ranges depending on the physical, chemical, or electrical properties sought. Thus, the polymers of this invention can be plastic or elastomeric, generally according to the identity and proportion of units derived from monomers making up the major part of the polymer composition, as known in the art.

Polymers of this invention can be prepared by any of the known processes for making fluoropolymers. Such processes can be conducted, for example, in an aqueous or non-aqueous medium, or in mixed media, i.e., hybrid processes, as well known in the art. As likewise well known in the art, dispersion or suspension processes can be employed, and processes can be conducted on a batch, semi-batch, or continuous basis.

When made by aqueous dispersion polymerization, the polymers of this invention can be used in dispersion form. The as-polymerized (raw) dispersion may be used as discharged from the reactor if it has adequate stability and/or wetting characteristics for the intended purpose. Alternatively, the raw dispersion can be adjusted by addition of surfactants, or concentrated and stabilized by techniques well known in the art. Other materials can be blended into the polymer dispersions for use in dispersion form, or such blends can be co-coagulated as a step toward dry blends or filled resins. Dispersion concentrations can vary over a broad range, such as from about 10–40 wt % solids as obtained from polymerization to about 70 wt % solids when concentrated, based on combined weight of polymer solids and aqueous medium. The fluoropolymer of the present invention as an aqueous dispersion is another embodiment of the invention.

Alternatively, after dispersion polymerization is complete and raw (as-polymerized) dispersion has been discharged from the reactor, traditional techniques known in the art (see U.S. Pat. No. 5,266,639, for example) can be used to recover the polymer solids from the aqueous polymerization medium. For example, such methods as coagulation by vigorous agitation, optionally with added electrolyte, or by freezing and thawing, followed by separation of the wet solids from the liquid and then by drying can be used.

As one skilled in the art will recognize, particles of the fluoropolymers of this invention can be used in many ways. Particles or particle aggregates, for example, can be sprinkled or dusted into place, can be applied to a surface from a dispersion or slurry, can be mixed with other powder or liquid as a binder or for other purposes, or can be distributed on a surface by one of several powder coating techniques such as electrostatic spraying or fluidized bed coating.

The fluoropolymers of this invention can be in solution in highly fluorinated solvents. Illustrative solvents are disclosed, for example, by Tuminello & Cavanaugh in U.S. Pat. No. 5,328,946 and by Morgan et al. in U.S. Pat. No. 5,397,829. Other solvents that can be used include fluorinated trialkyl amines such as perfluoro(dibutylmethyl)amine and perfluoro(triamyl)amine. Lower-melting polymers are more easily dissolved than higher-melting polymers, and amorphous polymers are even more easily dissolved. Solutions of the fluoropolymers of this invention in highly fluorinated solvents are another aspect of the invention. Perfluorinated compounds are preferred as solvents, but fluorinated compounds having up to about 12.5 atomic percent (at %) hydrogen and/or about 37.5 at % chlorine can be used. The concentration of polymer in the solutions of this invention can be at least 0.1 wt % and as much as 10 wt % and higher, 20 wt % and 30 wt %, depending on the solubility of the polymer in the solvent, based on combined weight of polymer and solvent. Since solution viscosity increases with polymer concentration, lower concentrations, such as 0.5–5 wt %, are preferred for many purposes.

Dispersions and solutions of the fluoropolymers of this invention can be used according to any of the techniques by which such systems are known to be used, including casting, dipping, painting and spraying, making it possible to achieve end results that could not be achieved with previously available perfluoropolymers or could be achieved only in less convenient ways. These results include any of the results for which polymer dispersions and solutions are used, such as coating, encapsulation, and impregnation. Normally, the dispersion or solution is deposited in place in the wet state, the deposit is dried, and the dried resin is fused or consolidated thermally.

The fluoropolymers of this invention in dispersion and solution can be used to make coatings on a broad range of substrate materials, including metals, semiconductors, glass, ceramics, refractory materials, dielectric materials, carbon or graphite, wood, and natural and synthetic polymers including plastics and elastomers. The substrates can be in a broad range of physical forms, including film or paper, foil, sheet, slab, coupon, wafer, wire, fiber, filament, cylinder, sphere, and other geometrical shapes, as well as in a virtually unlimited number of irregular shapes. These coatings can be useful for articles requiring anti-reflective, chemical resistant, release, lubricity, anti-staining, ice release, low dielectric constant, or reduced surface energy characteristics. Coatings can be applied by methods known in the art, including dipping, spraying, and painting. For plane substrates of suitable dimensions, spin coating can be employed. Porous substrates, including those made from fluoropolymer such as polytetrafluoroethylene, can also be coated or impregnated. These include, for example, screens, foams, microporous membranes, and woven and non-woven fabrics.

Coatings of the fluoropolymers of this invention can be a sole coating on a substrate, or a component of a multilayer coating. For example, a cyanate- or carbamate-containing fluoropolymer coating of this invention can be used as a first or primer, intermediate, or final (top) coating in a multilayer fluoropolymer coating system. The coatings of this invention include coatings resulting from several successive applications of dispersion or solution to increase coating thickness to desired levels.

Coatings of this invention can consist of the fluoropolymers of this invention alone, or of the fluoropolymers admixed with minor amounts of other materials either soluble in water or the solvent or dispersed in the coating dispersion or solution. A minor amount can be up to about 10 wt % based on the combined weight of fluoropolymer and additive.

EXAMPLES

Melting temperature ($T_m$) and glass transition temperature ($T_g$) were measured by differential scanning calorimetry (DSC), using a DuPont thermal analyzer. As is conventional, $T_m$ was taken as the peak of the melting endotherm for partially-crystalline polymers, while $T_g$ was taken as the point of slope change in the DSC trace for non-crystalline polymers.

Polymer composition was measured by high temperature $^{19}$F NMR spectroscopy using a GE NMR spectrometer. Temperature was such that the sample was in the melt state, that is, above $T_m$ for partially-crystalline samples and above $T_g$ for non-crystalline samples. Infrared spectroscopy was used to identify the —OCN (cyanate) and —O—(CO)—NH$_2$ (carbamate) groups.

Monomer compositions were determined by proton and $^{19}$F NMR, infrared spectroscopy (IR), and gas chromatography (GC).

Example 1

To a pre-dried flask were charged 9,9-dihydro-9-hydroxy-perfluoro-(3,6-dioxa-5-methyl-1-nonene) (EVE-OH, U.S. Pat. No. 5,059,720) (39.4 g, 0.10 mol) and cyanogen bromide (11.13 g, 0.105 mol) in acetone solvent (60 mL) with vigorous stirring. Triethylamine (11.11 g, 0.11 mol) was added slowly into the above solution. The reaction temperature was kept at around 0° C. by external cooling. After the addition was complete, the reaction mixture was stirred at 0° C. for 15 to 30 min, then was dumped into ice water. The bottom organic layer was separated, washed with water and distilled to give a clear, colorless liquid having a boiling point of 47° C. at 0.7 mmHg, and identified by infrared spectroscopy and $^{19}$F NMR as 9-cyanato-9,9-dihydroperfluoro-(3,6-dioxa-5-methyl-1-nonene) (EVE-OCN, formula above). Yield was 26 g (62%).

Example 2

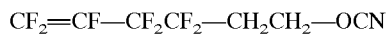

To a round bottom flask were charged EVE-OH (188 g, 0.477 mol) and cyanogen bromide (53.4 g, 0.503 mol) in acetone solvent (250 mL). While under vigorous stirring, triethylamine (50 g, 0.495 mol) was slowly added and the reaction temperature was controlled at around 0° C. by external cooling. After the addition was complete, the mixture was stirred at 0° C. for 30 min before pouring it into ice water. The bottom organic layer was separated, worked up as in Example 1, and distilled to give the liquid EVE-OCN product (139 g, 70% yield) having a boiling point of 48°–52° C. at 1 mmHg.

When CF$_2$═CF—CF$_2$CF$_2$—CH$_2$CH$_2$—OH (Example 2, U.S. Pat. No. 4,564,717) is used in the above procedure instead of EVE-OH, CF$_2$═CF—CF$_2$CF$_2$—CH$_2$CH$_2$—OCN is obtained as the cyanate (I).

Example 3

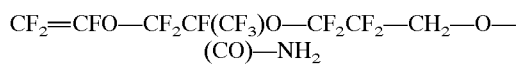

EVE-OCN (30 g, 0.0716 mole) was mixed with 8 mL of 6 N HCl and was stirred for 6 hr at ambient temperature. The EVE-OCN was mostly unchanged as indicated by $^{19}$F NMR, IR, and GC analyses. The temperature was then raised to 50° C. and after 2 hr the conversion of the starting material was complete. The bottom organic layer was separated, washed with water, and distilled to give 20.6 g (65.8% yield) of EVE-carbamate, formula above, as a clear, colorless liquid having a boiling point of 80°–84° C. at 2 mmHg. The EVE-carbamate structure was confirmed by $^{19}F$ and proton NMR and IR.

Example 4

Copolymerization of EVE-OCN with TFE

A 400 mL stainless steel shaker tube was charged with EVE-OCN (3 g) from Example 2, 1,1,2-trichloro-1,2,2-trifluoroethane (CFC-113, 150 g), and 4,4'-bis(t-butylcyclohexyl)-peroxy dicarbonate (0.03 g). The tube was sealed, cool-evacuated and tetrafluoroethylene (TFE, 50 g, 0.50 mol) was transferred into the tube. The tube was again sealed and heated at 60° C. for 4 hr with shaking. After cooling, the solvent was removed from the unloaded polymer solution and the resultant polymer was dried in a vacuum oven (150 mmHg ) at 100° C. for 24 hrs. A white polymer powder (47.5 g) was obtained. The polymer was thermally stable as indicated by thermogravimetric analysis and had a high melting temperature of 319.8° C. as measured by DSC. The polymer had molar composition of TFE/EVE-OCN=99.6/0.4 as determined by $^{19}F$ NMR spectroscopy at high temperature (melt state).

Example 5

Copolymerization of EVE-OCN with TFE and PDD

A 400 mL shaker tube was charged EVE-OCN (1.0 g), perfluoro-(2,2-dimethyl-1,3-dioxole) (20 g), CFC-113 (80 g) and 4,4'-bis(t-butyl-cyclohexyl)peroxy dicarbonate (0.02 g). The tube was sealed, cooled and evacuated, then tetrafluoroethylene (1.0 g) was transferred into the tube. The tube was sealed and heated at 60° C. for 4 hr under shaking. The unloaded polymer solution was first dried to remove residual solvent, washed with warm water, and then dried in a vacuum oven (150 mmHg) for 24 hr at 100° C. to yield a white polymer powder (12.5 g). This polymer had a $T_g$ of 208.5° C. as determined by DSC. The molar composition of this polymer was determined to be PDD/TFE/EVE-OCN =97.19/2.55/0.26 by $^{19}F$ NMR spectroscopy at high temperature (melt state). The presence of the cyanato group was confirmed by infrared spectroscopy. The inherent viscosity of the polymer was 1.964 dL/g as measured in perfluorinated cyclic ether (Fluorinert® FC-75, 3M Company) at 25° C.

A thin film was obtained by casting on a glass plate from a 2–3 wt % solution of this polymer in FC-75. After heating at 150° C. for 1.5 hr, the highly transparent film exhibited very strong adhesion to the glass surface. This observation indicates the strong adhesive bond achievable with the —OCN functional group in fluoropolymers.

Example 6

Copolymerization of EVE-OCN with TFE and PPVE

Following the general procedure of Example 4, EVE-OCN (3 g), perfluoro(propyl vinyl ether) (PPVE, 6 g), and TFE (50 g) were polymerized in CFC-113 (200 g) using 0.05 g of 4,4'-bis(t-butylcyclohexyl)peroxy dicarbonate to initiate the polymerization. After polymerization at 60° C. for 4 hr, the polymerization product was worked up and a white polymer powder (40.5 g) was obtained. The polymer had $T_m$=312.4° C. by DSC and molar composition of TFE/ PPVE/EVE-OCN=98.48/0.91/0.61 by $^{19}F$ NMR spectroscopy as described above. The presence of the cyanato group was confirmed by infrared spectroscopy.

Example 7

Copolymerization of EVE-OCN with TFE and PMVE

A 400 mL stainless steel shaker tube was charged with de-ionized water (260 mL), ammonium perfluorooctanoate surfactant (C-8, 2.0 g), disodium phosphate (0.5 g), EVE-OCN (2.0 g) and ammonium persulfate (APS, 0.2 g). The tube was sealed and cool-evacuated. Then TFE (45 g) and perfluoro(methyl vinyl ether) (PMVE, 27 g) were transferred into the tube. The tube was sealed and heated at 70° C. for 4 hr. After cooling, the resulting dispersion was coagulated with dilute nitric acid. The polymer solids were collected by filtration, then washed thoroughly with warm water. After drying overnight in a vacuum oven (150 mmHg) at 100° C., a white polymer powder (50.5 g) was obtained. The polymer had a $T_g$ of –1.7° C., and its molar composition was determined to be TFE/PMVE/EVE-OCN=79.46/20.29/ 0.25 by $^{19}F$ NMR spectroscopy in the polymer melt state.

Example 8

Copolymerization of EVE-OCN with TFE and PMVE

The procedure of Example 6 was generally followed, except that the amount of EVE-OCN was 1.0 g, the amount of TFE was 48 g, and the amount of PMVE was 15 g. The product obtained was 56.5 g of a white polymer powder. This polymer exhibited a broad melting endotherm with peak at 249.8° C., and the molar composition of this polymer was determined to be TFE/PMVE/EVE-OCN=87.14/12.64/ 0.22 by $^{19}F$ NMR spectroscopy in the polymer melt state.

Example 9

Copolymerization of EVE-OCN with TFE and PPVE

The procedure of Example 6 was generally followed, except that the amount of EVE-OCN was 3.0 g and perfluoro(propyl vinyl ether) (PPVE, 7.0 g) was used in the pre-charge instead of PMVE after evacuation, to obtain 53.0 g of white polymer powder. This polymer had $T_m$=309.7° C. (second heat) and molar composition of TFE/PPVE/EVE-OCN=96.48/2.63/0.89 by $^{19}F$ NMR spectroscopy (melt state).

Example 10

Copolymerization of EVE-OCN with TFE and PPVE

A one-liter stirred reactor was charged with deionized water (550 mL), C-8 (4.0 g), disodium phosphate (1.0 g), EVE-OCN (6.0 g), PPVE (14.0 g), and APS (0.2 g). The reactor was purged with nitrogen, cooled and evacuated, and then TFE (100 g) was transferred into the reactor. Polymerization was carried out at 70° C. for 6 hr. The dispersion product of polymerization was worked up generally as in Example 6 to obtain 92.7 g of white polymer powder. This polymer had $T_m$=321.4° C. and molar composition of TFE/ PPVE/EVE-OCN=96.9/2.32/0.78 by $^{19}F$ NMR spectroscopy.

Example 11

Neat EVE-OCN and 8-CNVE monomers were charged into separate NMR tubes and their high temperature reactions were monitored by $^{19}$F NMR spectroscopy. It was observed that EVE-OCN started to gel at 175° C., and completely gelled in 15 min at 200° C. The appearance of a new absorption band at 1587 cm$^{-1}$ in the infrared spectrum indicated triazine formation during this thermal process. In contrast, 8-CNVE is largely unreacted even at 250° C. This comparison indicates the superior reactivity of EVE-OCN over 8-CNVE.

Example 12

TFE/PEVE copolymer with EVE-OCN in shell

In a horizontal 1-gal (3.8-L) autoclave equipped with a paddle agitator, 2300 mL of demineralized water were deareated by evacuation and purging with nitrogen. While under vacuum, 25 g of a 20 wt % solution of C-8, 17 mL of perfluoro(ethyl vinyl ether) (PEVE) and 1 g of ethane were added. The temperature was increased to 80° C. and the pressure was increased to 300 psig (2.17 MPa) by addition of TFE. An initial initiator charge of 60 mL of a 2 g/L aqueous solution of APS was added. At kickoff, as determined by a 5 psi (0.03 MPa) pressure drop, a feed of a mixture of TFE and PEVE in the ratio TFE:PEVE=97.1:2.9 by weight was begun to maintain pressure at 300 psig. Also, an addition of 0.5 mL/min of the same initiator solution was begun. When 600 g of TFE/PEVE mixture had been added after kickoff, 10 mL of EVE-OCN were added. After 650 g of TFE/PEVE mixture had been added after kickoff, all feeds were stopped and the pressure was allowed to drop to 150 psig (1.1 MPa). The reactor was vented and cooled, and the product dispersion was collected. Solids content of the dispersion was 22.2 wt %. An aliquot of the dispersion was diluted with an equal volume of demineralized water and shear coagulated in a Waring blender. The wet resin was rinsed with demineralized water, and dried at 150° C. The product resin contained 2.44 wt % of PEVE and 0.83 wt % of units derived from EVE-OCN but present with carbamate functionality, as determined by Fourier transform infrared (FTIR) spectroscopy. I.e., under these polymerization conditions, all detectable —OCN was converted to —O—(CO)—NH$_2$. The melt flow rate, as measured at 372° C. with a 1060 g weight, was 11.5 g/10 min. Melting point was 309° C.

A portion of the powder solids was suspended in isopropanol to form a thin slurry (5 g in 15 mL alcohol). The slurry was coated onto an aluminum sheet using an 8-mil (0.2-mm) draw bar and the alcohol was allowed to air dry. Pellets of a TFE/PPVE copolymer resin that has been chemically modified to enhance purity and improve thermal stability (Teflon® PFA fluoropolymer resin grade 440 HP, DuPont) were placed on the coating in a 0.010-inch (0.25-mm) thick and 6-inch (15.2-cm) square chase having a 4-inch (10.2-cm) square opening and another aluminum sheet placed on top of the construction. The sandwich was compression molded at 350° C. in an 8-min cycle (3 min at platten contact, 2 min to increase ram force to 5000 lb {2273 kg}, and 3 min at 5000 lb), removed from the press and quenched in ice water. The aluminum sheet on the 440 HP side of the construction easily peeled from the resin surface. The powder treated side remained adhered to the aluminum. A 1-inch (2.54-cm) wide strip of this adhered side was cut and subjected to peel testing in a tensile tester (Instron). Average peel strength was 2.0 lb/inch (360 g/cm), showing the enhanced adhesion of the polymer of this invention.

Example 13

TFE/PEVE copolymer with EVE-carbamate in shell

The polymerization procedure of Example 12 was essentially repeated, except that EVE-carbamate was used as the functional monomer instead of the EVE-OCN, and the amount was 9.6 mL instead of 10 mL. Solids content of the dispersion was 20.3 wt %. An aliquot of the dispersion was placed into a freezer and allowed to freeze solid overnight. Upon thawing, the resulting suspension was filtered through Whatman 541 paper on a Bucherer funnel and washed three times with demineralized water. The solids were then dried overnight at 100° C. The dried product resin contained 6.65 wt % of PEVE and 1.07 wt % of units derived from EVE-carbamate. Melting point was 289° C. The copolymer resin powder was used to produce a laminate as in Example 12, except that a #24 wire-wound rod (R. D. Specialties, Inc.) was used instead of the draw bar, which gave a peel strength of 480 g/cm.

What is claimed is:

1. A compound having the formula

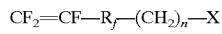

$$CF_2=CF-R_f-(CH_2)_n-X$$

wherein —X is —OCN or —O—(CO)—NH$_2$, n is 1–3, and R$_f$ is perfluoroalkyl or perfluoroalkoxy having 1–20 carbon atoms.

2. The compound of claim 1, wherein n is 1.

3. The compound of claim 2, wherein R$_f$ is O—(CF$_2$)$_m$ and m is 2–4.

4. The compound of claim 2, wherein R$_f$ is [O—CF$_2$CF(CF$_3$)]$_k$—O—CF$_2$CF$_2$ and k is 1–5.

5. The compound of claim 4, wherein k is 1.

* * * * *